(12) United States Patent
Bae et al.

(10) Patent No.: US 10,124,321 B2
(45) Date of Patent: Nov. 13, 2018

(54) CARBON NITRIDE HETEROGENEOUS CATALYST CONTAINING RHODIUM, METHOD FOR PREPARING THE SAME, AND METHOD FOR PREPARING ACETIC ACID USING THE SAME

(71) Applicant: Korea Research Institute of Chemical Technology, Daejeon (KR)

(72) Inventors: Jong Wook Bae, Gyeonggi-do (KR); Tae Sun Chang, Daejeon (KR); Beom Sik Kim, Daejeon (KR); Jae Hyun Park, Gyeonggi-do (KR); Ji Soo Nam, Incheon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 0 days.

(21) Appl. No.: 15/881,170

(22) Filed: Jan. 26, 2018

(65) Prior Publication Data

US 2018/0147565 A1 May 31, 2018

Related U.S. Application Data

(63) Continuation-in-part of application No. PCT/KR2016/008212, filed on Jul. 27, 2016.

(30) Foreign Application Priority Data

Jul. 27, 2015 (KR) ........................ 10-2015-0105818

(51) Int. Cl.
| | |
|---|---|
| *C07C 51/12* | (2006.01) |
| *C07C 67/36* | (2006.01) |
| *B01J 23/46* | (2006.01) |
| *B01J 37/08* | (2006.01) |
| *B01J 32/00* | (2006.01) |
| *B01J 27/24* | (2006.01) |
| *B01J 35/00* | (2006.01) |
| *B01J 35/10* | (2006.01) |

(52) U.S. Cl.
CPC ............ *B01J 23/464* (2013.01); *B01J 23/46* (2013.01); *B01J 27/24* (2013.01); *B01J 32/00* (2013.01); *B01J 35/0006* (2013.01); *B01J 35/1009* (2013.01); *B01J 35/1014* (2013.01); *B01J 37/08* (2013.01); *B01J 37/084* (2013.01); *B01J 37/086* (2013.01); *C07C 51/12* (2013.01); *C07C 67/36* (2013.01)

(58) Field of Classification Search
CPC .......... C07C 51/12; B01J 23/46; B01J 23/464
See application file for complete search history.

(56) References Cited

U.S. PATENT DOCUMENTS 4,792,620 A * 12/1988 Paulik ................. B01J 31/0231
560/232

FOREIGN PATENT DOCUMENTS

| CN | 103586064 A | | 2/2014 |
|---|---|---|---|
| KR | 1020160080379 A | | 7/1916 |
| KR | 100176417 B1 | | 3/1999 |
| KR | 1020020092934 A | | 12/2002 |
| KR | 1020060122944 A | | 11/2006 |
| KR | 101540198 B1 | | 7/2015 |
| KR | 1020150014575 | * | 7/2015 |

OTHER PUBLICATIONS

Norskov et al, Nature Chemistry, Towards the Computational Design of Solid Catalysts, 2009, 1, pp. 37-46 (Year: 2009).*
Zhang et al (International Journal of Hydrogen Energy, Influence of Rh nanoparticle size and composition on the photocatalytic water splitting performance of Rh/graphitic carbon nitride, 2014, 39, pp. 11537-11546. (Year: 2014).*
Budiman, Anatta Wahyu, et al. "Review of acetic acid synthesis from various feedstocks through different catalytic processes", Catalysis Surveys from Asia, 2016, 20, 3.
Di Noto, V. et al. "Synthesis, structure and electrochemical performance of new Pt-Rh carbon nitride electrocatalysts for the oxygen reduction reaction", 211th ECS Meeting, 2007, 110.
Zhang, Yi et al. "Infuence of Rh nanoparticle size and composition on the photocatalytic water splitting performance of Rh/graphitic carbon nitride", International Journal of Hydrogen Energy, 2014, 39, 22.
International Search Report and Written Opinion for PCT/KR2016/008212, dated Oct. 31, 2016.

* cited by examiner

*Primary Examiner* — Paul A Zucker
(74) *Attorney, Agent, or Firm* — Norton Rose Fulbright US LLP

(57) ABSTRACT

A carbon nitride heterogeneous catalyst containing rhodium, a method for preparing the catalyst, and a method for preparing acetic acid using the catalyst is disclosed. The heterogeneous catalyst is characterized in that the rhodium metal is contained in carbon nitride which is a support insoluble in a liquid solvent, such as water or alcohol. Thus, the catalyst can easily be separated from a resulting product even by a simple process such as filtration. Accordingly, the carbon nitride heterogeneous catalyst exhibits excellent long-term stability and activity by being capable of overcoming the disadvantages of the method using a conventional homogeneous catalyst and minimizing the phenomenon of rhodium leaching, compared to the results of the conventional homogeneous catalytic reactions. The catalyst can thus be effectively used for the preparation of acetic acid by a carbonylation reaction between methanol and carbon monoxide.

18 Claims, 2 Drawing Sheets

[FIG. 3]
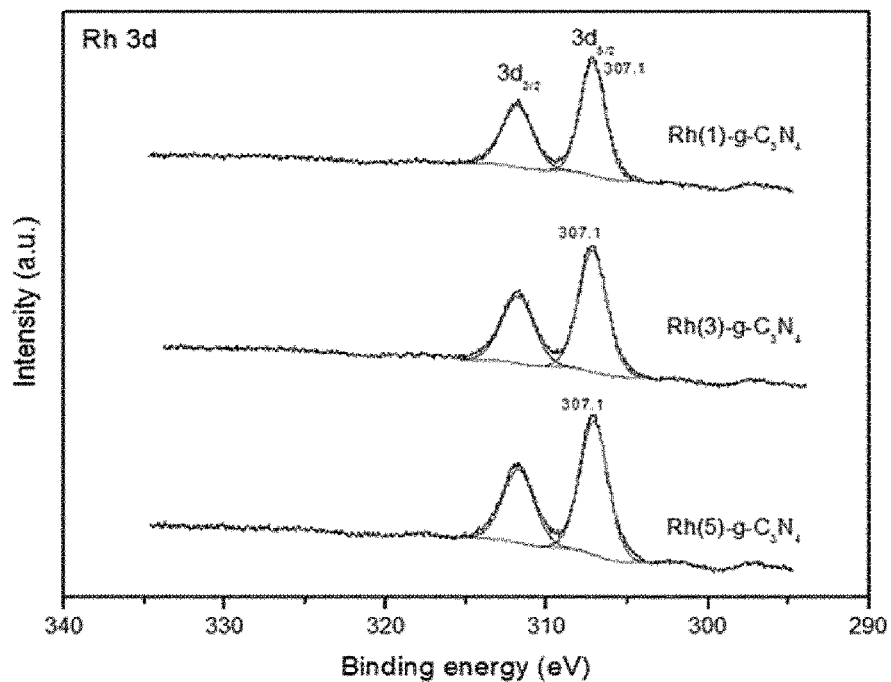
[FIG. 4]
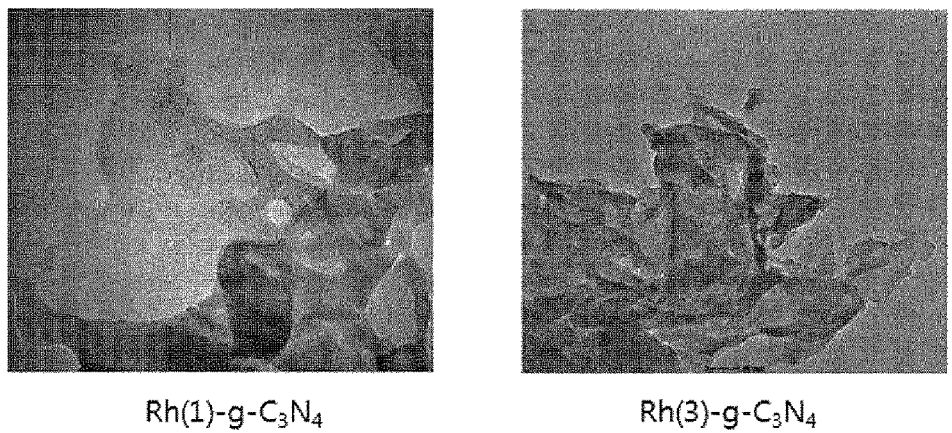
Rh(1)-g-C₃N₄          Rh(3)-g-C₃N₄

CARBON NITRIDE HETEROGENEOUS CATALYST CONTAINING RHODIUM, METHOD FOR PREPARING THE SAME, AND METHOD FOR PREPARING ACETIC ACID USING THE SAME

CROSS-REFERENCE TO RELATED APPLICATIONS

This application is a continuation-in-part of International Application No. PCT/KR2016/008212 filed Jul. 27, 2016, which claims the benefit of priority of Republic of Korea Patent Application No. 10-2015-0105818 filed Jul. 27, 2015. The entire contents of each of the above-referenced applications are incorporated into the present application by reference.

FIELD OF THE INVENTION

The present invention relates to a carbon nitride heterogeneous catalyst containing rhodium, a method of preparing the catalyst, and a method for preparing carboxylic acid using the catalyst.

DESCRIPTION OF RELATED ART

Acetic acid is a representative carboxylic acid and is also a major raw material for the production of vinyl acetate monomers, terephthalic acid, etc., in modern industrialized processes. The general method for synthesizing acetic acid on an industrial scale is to directly synthesize acetic acid by a carbonylation reaction between methanol and carbon monoxide as shown in Reaction Scheme 1 below.

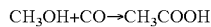
[Reaction Scheme 1]
$$CH_3OH+CO \rightarrow CH_3COOH$$

The carbonylation reaction between methanol and carbon monoxide is carried out in a liquid phase which mostly uses a homogeneous catalyst, and acetic acid has been prepared using a metal complex catalyst and methyl iodide as a co-catalyst, or using a rhodium or iridium complex catalyst. Although these catalysts show high selectivity on acetic acid, they have problems in that the use of iodide as a co-catalyst can cause corrosion and recovery of catalytic components and separation of the product from a single phase are extremely difficult thus requiring an additional process, or leaching, which refers to a phenomenon that a precious metal such as rhodium and iridium is adsorbed to a reaction product, melted, and released therefrom, is occurred thereby significantly lowering the economy of the process.

In order to solve the above problems, a heterogeneous catalyst in which rhodium is immobilized to a poly(4-vinylpyridine) polymer support was developed and methanol carbonylation was performed using the catalyst. As a result, reusability and recovery of the catalyst were significantly improved compared to when carbonylation was performed using a conventional homogeneous catalyst. However, the method also has a problem in that the amount of rhodium, which is an active component of the reaction, per an equal amount of catalyst is low and thus results in relatively low conversion of methanol as a reactant and low selectivity on acetic acid.

Additionally, since the process of using the polymer, poly(4-vinylpyridine), as a support causes deactivation of a catalyst due to thermal modification of the catalyst, the operation under high-temperature and high-pressure conditions becomes difficult and thus there is little room for improvement with regard to studies relating to merits and demerits that may occur in connection with various process parameters.

Under the circumstances, for minimizing the decrease of activity of the catalyst present between rhodium and a support or maximizing the improvement phenomenon, studies using metal oxides or novel polymers instead of poly(4-vinylpyridine) are underway.

SUMMARY OF THE INVENTION

In order to solve the problems of homogeneous catalysts, which are known to require an additional process due to the difficulty in the separation of the catalyst and reaction products because all materials in the conventional carbonylation reaction system are proceeded in the same phase while simultaneously increasing the catalytic activity effectively by preventing the leaching of the conventional heterogeneous catalysts, the present invention provides a carbon nitride heterogeneous catalyst containing rhodium as a catalyst for alcohol carbonylation, a method for preparing the catalyst, and additionally, a method for preparing acetic acid using the heterogeneous catalyst.

A first aspect of the present invention provides a catalyst for an alcohol carbonylation, comprising carbon nitride support and rhodium dispersed therein.

A second aspect of the present invention provides a method for preparing the catalyst of the first aspect, which includes preparing carbon nitride where rhodium is dispersed therein by heating a rhodium precursor and melamine resin serving as a carbon source at a temperature of 500° C. to 550° C. under a nitrogen atmosphere.

A third aspect of the present invention provides a method of preparing carboxylic acid, which includes injecting a carbon monoxide-containing gas to a methanol-containing solution at a pressure of 10 bar to 200 bar and reacting at a temperature of 50° C. to 200° C. in the presence of a carbon nitride heterogeneous catalyst containing rhodium.

A fourth aspect of the present invention provides a method of producing carboxylic acid by carbonylating alcohol in the presence of a composite catalyst comprising carbon nitride support and rhodium dispersed therein Hereinafter, the present invention will described more specifically in various aspects with reference to various embodiments.

The present invention relates to a catalyst used in a reaction for preparing carboxylic acid by carbonylation of an alcohol with carbon monoxide, and provides a heterogeneous catalyst comprising carbon nitride support and rhodium contained therein.

The conventional catalysts used in alcohol carbonylation for preparing acetic acid are mostly those in which an active material is immobilized on a support. However, in the rhodium-containing carbon nitride heterogeneous catalyst of the present invention, unlike the conventional catalysts, the support itself plays the role of a catalyst. Specifically, the heterogeneous catalyst of the present invention contains rhodium in the carbon nitride support, and more specifically, the rhodium is dispersed and positioned inside of the carbon nitride. In this case, it is expected that the reactivity of a catalyst can be improved by the increase of dispersibility of the metal rhodium positioned inside of the carbon nitride network and the catalyst can be stabilized, and there is also an advantage in that the catalyst can easily be recovered by a simple process such as simple filtration or flotation due to the difference in phase with the reactants. Additionally, the stability of the catalyst can be increased by reducing the leaching level of the precious metal, rhodium, and in a long-term aspect, the catalytic function can be secured for a long period of time.

In a case when rhodium is in electron transfer on a carbon nitride support, the bimetallic effect which can be expected from the activation of electron transfer. In this case, the high-yield production of acetic acid that could have been expressed under the conventional high-temperature and high-pressure conditions can be converted in relatively low-temperature and low-pressure conditions. As a result of the reaction, the selectivity on acetic acid can be increased and thus the catalyst can be effectively used for preparing acetic acid by a carbonylation reaction between an alcohol and carbon monoxide.

The present invention provides a composite catalyst for an alcohol carbonylation, comprising a first catalyst of carbon nitride support and a second catalyst of rhodium dispersed in the network of the carbon nitride support to reduce the leaching level of the rhodium in the alcohol carbonylation.

The alcohol according to the present invention may be methanol or ethanol, and preferably methanol.

The rhodium may be contained in an amount of 0.1 wt % to 10 wt % based on the total weight of carbon nitride.

When the amount of rhodium is lower than 0.1 wt %, the activity of the catalyst may below. In contrast, when the amount of rhodium exceeds 10 wt %, the specific surface area of the catalyst may be reduced and the manufacturing cost for the catalyst may increase due to the increase of the amount of the precious metal being used.

The catalyst according to the present invention may have a specific surface area in a range of 0.5 m$^2$/g to 100 m$^2$/g for securing the level of reaction activity of the catalyst for the carbonylation reaction.

The carbon nitride according to the present invention is a carbon nitride having a chemical formula of $C_3N_4$, and it may be graphite carbon nitride, α-carbon nitride, β-carbon nitride, cubic carbon nitride, or pseudocubic carbon nitride, and preferably, graphite carbon nitride.

Meanwhile, the graphite carbon nitride may be synthesized in the form of films, hollow spheres, and nanotubes, etc. Recently, graphitic carbon nitride, in which macro-sized spherical pores are aligned regularly and are interconnected in a three-dimensional manner by means of meso-sized connecting pores while simultaneously having a high content of nitrogen is used, but graphitic carbon nitride is not limited thereto.

The carbon nitride in the heterogeneous catalyst of the present invention has a large amount of internal Lewis acid site and can thus lead the catalyst-reactant interaction from the electron transfer. As a result, the carbon nitride in the heterogeneous catalyst of the present invention can play the role of a pseudo-metal and the heterogeneous catalyst of the present invention exhibits a catalytic activity equal to the reaction of a homogeneous catalyst because rhodium as a reaction active material is distributed inside.

The characteristic of holding a large amount of Lewis acid site means that it has a positive effect not only on the role of carbon nitride as a catalyst but also on the adsorption to a metal thus being capable of uniformly dispersing the rhodium element as an active material within the support, and due to the characteristic of holding a large amount of Lewis acid site, the aggregation or leaching of the rhodium positioned inside of the support can be inhibited.

Accordingly, the heterogeneous catalyst of the present invention, in which rhodium as an active material is incorporated into and immobilized on the carbon nitride support, is inhibited with respect to its deactivation from the catalytic aspect of the rhodium element and thus a stable and long-term function of a catalyst can be secured.

In the present invention, a catalyst was prepared so that the catalytic activity could be exhibited in a state that the rhodium is incorporated into or immobilized on the support, and thereby a rhodium-containing carbon nitride heterogeneous catalyst to be used for preparing acetic acid by a carbonylation reaction was obtained.

For the preparation of the catalyst, a heterogeneous catalyst was prepared by a method which includes heating melamine resin, which is used as a carbon source, and a rhodium precursor at a temperature of 500° C. to 550° C. and a pressure of 2 bar to 5 bar in an atmosphere of nitrogen (flow rate: 50 cc/min) thereby immobilizing the rhodium metal on the structure consisting of nitrogen and carbon.

Meanwhile, at the early stage of synthesizing a catalyst, that is, a precursor containing an active material is synthesized before heat treatment and then heat-treated thereby preventing the deactivation of the catalyst that can occur from the self-aggregation of rhodium, which is an active material.

The carbon nitride support may be prepared by thermal condensation during the preparation process and heat-treatment may be applied thereto while slowly increasing the temperature with a temperature gradient.

Specifically, the rhodium-containing carbon nitride support may be prepared as follows: melamine resin in a powder form, which is used as a carbon source, is heated at a rate of about 1° C./min to about 3° C./min to reach a reaction temperature of 200° C. to 250° C. under a nitrogen atmosphere, and the temperature is maintained thereat for 20 minutes to 40 minutes; then, the melamine resin is heated at a rate of about 1° C./min to about 3° C./min to reach a reaction temperature of 300° C. to 350° C. and the temperature is maintained thereat for 20 minutes to 40 minutes; and finally, the melamine resin is heated at a rate of about 1° C./min to about 3° C./min to reach a reaction temperature of 500° C. to 550° C. and the temperature is maintained thereat for 200 minutes to 300 minutes.

A carbon nitride support containing rhodium in powder form may be prepared by rearrangement of carbon and nitrogen by subjecting melamine resin to condensation and thermal-decomposition via heating rate and heating temperature gradient during the process of preparing the support.

The rhodium precursor according to the present invention may be at least one kind selected from the group consisting of rhodium chloride ($RhCl_3$), rhodium nitrate ($Rh(NO_3)_3$), dichloro tetracarbonyl dirhodium ($Rh_2(CO)_4Cl_2$), (acetylacetonato) dicarbonyl rhodium ($Rh(CO)_2(C_5H_7O_2)$), acetylacetonato bis(ethylene)rhodium ($C_9H_{15}O_2Rh$), and dicarbonyl (pentamethyl cyclopentadienyl) rhodium ($C_{12}H_{15}O_2Rh$).

Additionally, as the nitrogen and carbon precursors according to the present invention, at least one kind of a precursor selected from the group consisting of cyanamide ($CH_2N_2$), dicyanamide ($C_2HN_3$), cyanuric chloride ($C_3N_3Cl_3$), 2-amino-4,6-dichloro-1,3,5-triazine ($C_3H_2Cl_2N_4$), and tricyanomelaminate salts, and a combination thereof may be used, in addition to melamine ($C_6H_6N_6$) used in the present invention.

The carbon nitride according to the present invention may be at least one kind of a carbon nitride selected from the group consisting of graphite carbon nitride, α-carbon nitride, β-carbon nitride, cubic carbon nitride, and pseudocubic carbon nitride.

The present invention may provide a method for preparing carboxylic acid by performing a carbonylation reaction between methanol and carbon monoxide using a catalyst according to the present invention. Preferably, the method for preparing acetic acid may include reacting at a temperature of 50° C. to 200° C. by injecting a carbon monoxide-containing gas into an alcohol-containing solution at a pressure of 10 bar to 200 bar in the presence of the catalyst according to the present invention.

In an exemplary embodiment, the present invention provides a method for preparing a carbon nitride heterogeneous catalyst containing rhodium, which includes preparing a carbon nitride support containing rhodium by heating a rhodium precursor and melamine resin, which was used as carbon source, at a temperature of 500° C. to 550° C. under a nitrogen atmosphere, so that the rhodium could be dispersed and positioned inside of the carbon nitride.

As described above, the carbonylation reaction between methanol and carbon monoxide using the catalyst according to the present invention has an advantage in that the reaction can be performed in a relatively mild condition, i.e., at a pressure of 10 bar to 200 bar by injecting a carbon monoxide-containing gas thereto.

In the present invention, the methanol-containing solution may be one that contains methanol as a reactant and iodomethane as co-catalyst and water. In particular, the mixing ratio between methanol:iodomethane:water may be in a range of 10 to 80:10 to 60:10 to 30 based on weight.

In the present invention, the carbon monoxide-containing gas may be a mixed gas of carbon monoxide and nitrogen. In particular, the mixing molar ratio between carbon monoxide and nitrogen may be in a range of 7 to 9:1 to 3.

In an exemplary embodiment of the present invention, the carbonylation reaction between methanol and carbon monoxide was performed in a 125 mL batch-type autoclave. The reactants used in the carbonylation reaction were 8 mL of methanol, 10 mL of iodomethane ($CH_3I$) as a reaction co-catalyst, 2 mL of distilled water, and 0.1 g of the prepared heterogeneous catalyst. For the preparation of the atmosphere of the reaction performed at high pressure, carbon monoxide (a reactant) was mixed with nitrogen (an internal standard material) in a 90:10 molar ratio (carbon monoxide:nitrogen) and the mixed gas was injected at a pressure of up to 40 bar to prepare the reaction. Then, the heating process was performed until the internal temperature of the reactor reached 135° C. while stirring the reactants and co-catalyst at 100 rpm. When the internal temperature of the reactor reached 135° C., the heating was stopped and the reaction was performed after increasing the stirring speed to 300 rpm.

In the present invention, the molar ratio between the reactants, methanol and carbon monoxide, is preferably 0.6 or higher, and more preferably maintained in a range of 0.6 to 10.0 for the improvement of reaction rate and selectivity on acetic acid.

The heterogeneous catalyst containing rhodium in a carbon nitride support according to the present invention is characterized in that, unlike a conventional homogeneous catalytic reaction in which reactants and a catalyst are in the same phase, the rhodium metal is contained in carbon nitride which is a support insoluble in a liquid solvent, such as water or alcohol, and thus, the catalyst can easily be separated from a resulting product even by a simple process such as filtration. Accordingly, the carbon nitride heterogeneous catalyst containing rhodium of the present invention exhibits excellent long-term stability and activity by being capable of overcoming the disadvantages of the method using a conventional homogeneous catalyst and minimizing the phenomenon of rhodium leaching, compared to the results of the conventional homogeneous catalytic reactions, and thus, can be effectively used for the preparation of acetic acid through carbonylation reaction between methanol and carbon monoxide.

BRIEF DESCRIPTION OF DRAWINGS

FIG. 3 shows X-ray photoelectron spectroscopy (XPS) graph of heterogeneous Rh-g-$C_3N_4$ catalysts according to the present invention.

FIG. 4 shows TEM images of Rh-g-$C_3N_4$ catalysts according to the present invention.

DETAILED DESCRIPTION OF THE INVENTION

Figure 1:
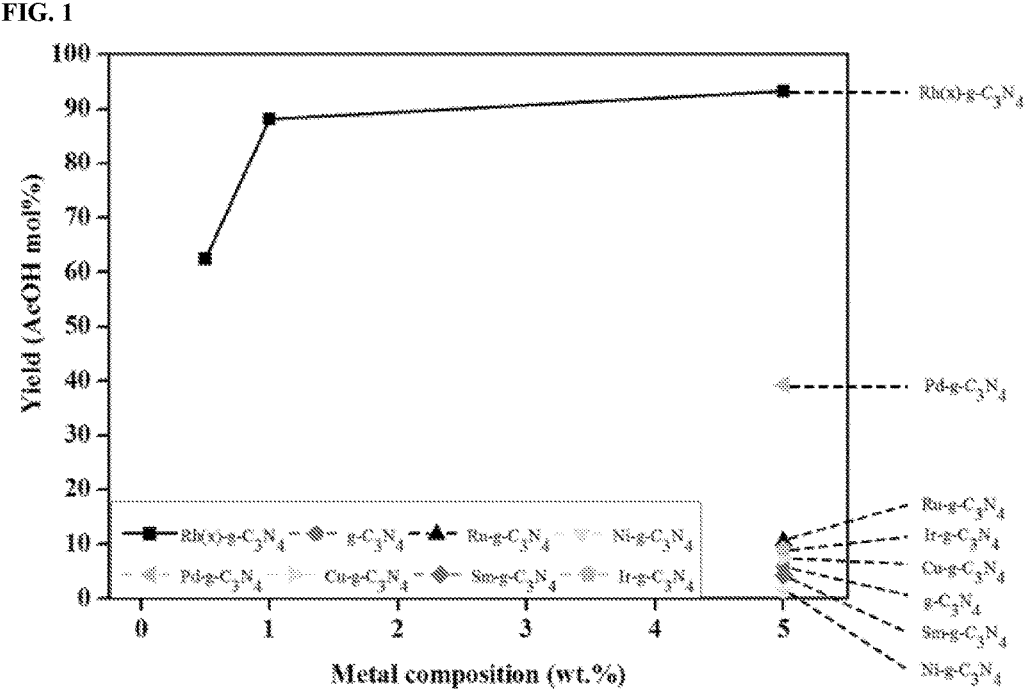
FIG. 1 shows a graph illustrating the yield obtained using a catalyst according to an exemplary embodiment of the present invention.

Hereinafter, the present invention will be described in more detail with reference to the following Examples. However, these Examples are for illustrative purposes only and the scope and contents of the present invention should not be reduced or limited by these Examples. Furthermore, it will be obvious that one of ordinary skill in the art can easily employ the present invention into practice with respect to the present invention in which experimental results are not specifically disclosed, based on the detail of the present invention including Examples provided herein below, and all such modifications and alterations should also belong to the scope of the appended claims.

EXAMPLES

Example 1: Preparation of a Heterogeneous Catalyst, Rh(0.5)-g-$C_3N_4$

Powder form of melamine (2.985 was mixed with distilled water (50 mL) and a solution (0.421 g), in which rhodium nitrate ($Rh(NO_3)_3$, 10 wt %) was dissolved in 10 wt % of nitric acid, was added thereto and the mixture was stirred at a rate of 180 rpm/min in a constant-temperature water bath maintained at room temperature. After stirring for 2 hours, the resultant was subjected to drying under reduced pressure while simultaneously increasing the temperature of the constant-temperature water bath to 60° C. The solution, upon completion of drying under reduced pressure, was added into a circulating dryer kept at 80° C. and dried for at least 12 hours to obtain a melamine-rhodium nitrate precursor in the form of reddish-brown powder. The precursor was added into a tube reactor and subjected to a thermal reaction while flowing a nitrogen gas thereinto at a rate of 50 mL/min. For the thermal reaction, the temperature of the tube reactor was increased from room temperature to 250° C. at a rate of 1.9° C./min, maintained at 250° C. for 30 minutes, increased from 250° C. to 350° C. at a rate of 1.7° C./min, and maintained at 350° C. for 30 minutes. Then, the temperature was sequentially increased from 350° C. to 550° C. at a rate of 3.3° C./min and maintained at 550° C. for 240 minutes. As a result, a rhodium-containing carbon nitride catalyst, in which rhodium metal (0.5 wt %) was positioned in a carbon nitride support, was prepared in the form of dark reddish-brown powder by the slow thermal condensation.

Example 2: Preparation of a Heterogeneous Catalyst, Rh(1)-g-$C_3N_4$

A heterogeneous catalyst was prepared in the same manner as in Example 1, except that the amount of rhodium nitrate and melamine used in Example 1 was changed to 0.843 g of rhodium nitrate and 2.970 g of melamine so that the rhodium element could be contained in an amount of 1 wt % based on the total amount of the heterogeneous catalyst. The catalyst prepared by the method of Example 2 was indicated as Rh(1)-g-$C_3N_4$.

Example 3: Preparation of a Heterogeneous Catalyst, Rh(5)-g-$C_3N_4$

A heterogeneous catalyst was prepared in the same manner as in Example 1, except that the amount of rhodium nitrate and melamine used in Example 1 was changed to 2.808 g of rhodium nitrate and 1.90 g of melamine so that the rhodium element could be contained in an amount of 5 wt % based on the total amount of the heterogeneous catalyst and the catalyst had a specific surface area of 7.032 $m^2/g$. The catalyst prepared by the method of Example 3 was indicated as Rh(5)-g-$C_3N_4$.

Comparative Example 1: Preparation of a Heterogeneous Catalyst, g-$C_3N_4$

A heterogeneous catalyst was prepared in the same manner as in Example 1, except that only melamine was heat-treated without adding any metal precursor at all. The catalyst prepared by the method of Comparative Example 1 was indicated as g-$C_3N_4$.

Comparative Example 2: Preparation of a Heterogeneous Catalyst, Sm-g-$C_3N_4$ A heterogeneous catalyst was prepared in the same manner as in Example 1, except that rhodium nitrate used as a metal precursor in Example 1 was replaced with samarium nitrate hexahydrate ($Sm(NO_3)_3 \cdot 6H_2O$) and the amount used was changed to 1.035 g of samarium nitrate hexahydrate and 6.65 g of melamine so that the samarium element could be contained in an amount of 5 wt % based on the total amount of the heterogeneous catalyst. The catalyst prepared by the method of Comparative Example 2 was indicated as Sm(5)-g-$C_3N_4$.

Comparative Example 3: Preparation of a Heterogeneous Catalyst, Ni-g-$C_3N_4$ A heterogeneous catalyst was prepared in the same manner as in Example 1, except that rhodium nitrate used as a metal precursor in Example 1 was replaced with nickel nitrate ($Ni(NO_3)_2 \cdot 6H_2O$) and the amount used was changed to 1.752 g of nickel nitrate and 6.65 g of melamine so that the nickel element could be contained in an amount of 5 wt % based on the total amount of the heterogeneous catalyst. The catalyst prepared by the method of Comparative Example 3 was indicated as Ni(5)-g-$C_3N_4$.

Comparative Example 4: Preparation of a Heterogeneous Catalyst, Cu-g-$C_3N_4$ A heterogeneous catalyst was prepared in the same manner as in Example 1, except that rhodium nitrate used as a metal precursor in Example 1 was replaced with kappa nitrate ($Cu(NO_3)_2 \cdot 3H_2O$) and the amount used was changed to 1.920 g of kappa nitrate and 9.50 g of melamine while simultaneously changing the temperature of the constant-temperature water bath to 50° C. so that the copper element could be contained in an amount of 5 wt % based on the total amount of the heterogeneous catalyst and the catalyst had a specific surface area of 4.585 $m^2/g$. The catalyst prepared by the method of Comparative Example 4 was indicated as Cu(5)-g-$C_3N_4$.

Comparative Example 5: Preparation of a Heterogeneous Catalyst, Pd-g-$C_3N_4$ A heterogeneous catalyst was prepared in the same manner as in Example 1, except that rhodium nitrate used as a metal precursor in Example 1 was replaced with palladium nitrate ($Pd(NO_3)_2$) and the amount used was changed to 10.829 g of palladium nitrate and 9.50 g of melamine while simultaneously changing the temperature of the constant-temperature water bath to 55° C. so that the palladium element could be contained in an amount of 5 wt % based on the total amount of the heterogeneous catalyst and the catalyst had a specific surface area of 4.486 $m^2/g$. The catalyst prepared by the method of Comparative Example 5 was indicated as Pd(5)-g-$C_3N_4$.

Comparative Example 6: Preparation of a Heterogeneous Catalyst, Ru-g-$C_3N_4$ A heterogeneous catalyst was prepared in the same manner as in Example 1, except that rhodium nitrate used as a metal precursor in Example 1 was replaced with ruthenium nitrosyl nitrate ($Ru(NO)(NO_3)_3$) and the amount used was changed to 16.667 g of ruthenium nitrosyl nitrate and 4.475 g of melamine so that the ruthenium element could be contained in an amount of 5 wt % based on the total amount of the heterogeneous catalyst. The catalyst prepared by the method of Comparative Example 6 was indicated as Ru(5)-g-$C_3N_4$.

Comparative Example 7: Preparation of a Heterogeneous Catalyst, Ir-g-$C_3N_4$ A heterogeneous catalyst was prepared in the same manner as in Example 1, except that rhodium nitrate used as a metal precursor in Example 1 was replaced with iridium chloride ($IrCl_3$) and the amount used was changed to 0.388 g of iridium chloride and 4.750 g of melamine while simultaneously changing the temperature of the constant-temperature water bath to 75° C. so that the iridium element could be contained in an amount of 5 wt % based on the total amount of the heterogeneous catalyst. The catalyst prepared by the method of Comparative Example 7 was indicated as Ir(5)-g-$C_3N_4$.

Experimental Example 1: Preparation of Acetic Acid by Carbonylation Reaction of Methanol The carbonylation reactions for preparing acetic acid from methanol and carbon monoxide using the heterogeneous catalysts prepared in Examples 1 to 3 and Comparative Examples 1 to 7 were performed in a 125 mL batch-type autoclave equipped with a Teflon container. The reactants used in the carbonylation reactions were 8 mL of methanol, 10 mL of iodomethane ($CH_3I$) as a reaction co-catalyst, 2 mL of distilled water, and 0.1 g of the prepared heterogeneous catalyst. For the preparation of the atmosphere of the reaction performed at high pressure, carbon monoxide (a reactant) was mixed with nitrogen (an internal standard material) in a 90:10 molar ratio (carbon monoxide nitrogen) and the mixed gas was injected at a pressure of up to 40 bar to prepare the reaction. Then, the heating process was performed until the internal temperature of the reactor reached 135° C. while stirring the reactants and co-catalyst at 100 rpm. When the internal temperature of the reactor reached 135° C., the heating was stopped and the carbonylation reaction was performed for 7 hours after increasing the stirring speed to 300 rpm. With regard to the reaction, the sample was collected at the time-point of 7 hours after the initiation of the reaction, when the conversion of methanol as a reactant became stabilized at a certain level, and the conversion of methanol and selectivity on products were calculated. The results are shown in Table 1 below.

active metals with regard to methanol carbonylation, are contained in the network, to the catalyst of Example 3 in which equal weight parts of rhodium are contained in the carbon nitride network, the Pd(5)-g-$C_3N_4$ catalyst of Comparative Example 5 showed a slightly lower yield compared to the catalytic activity of the rhodium carbon nitride, but the catalyst could be used in preparing acetic acid by methanol carbonylation due to little problem with regard to the leaching of metal components, whereas the Ru(5)-g-$C_3N_4$ catalyst of Comparative Example 6 showed a significant decrease of conversion of methanol and selectivity on acetic acid.

Comparing to the catalyst of Example 3 in which equal weight parts of an element were contained as described above, it was confirmed that the catalyst of Comparative Example 7 in which iridium is incorporated into the network

TABLE 1

| Category | Methanol Conversion (Carbon Mol %) | Yield of Acetic Acid (Mol %) | Selectivity (Mol %) | | | Leaching (%) |
| --- | --- | --- | --- | --- | --- | --- |
| | | | Acetic Acid | Methyl Acetate | Others | |
| Example 1 | 88.2 | 62.4 | 70.8 | 24.8 | 4.4 | — |
| Example 2 | 99.4 | 88.1 | 88.6 | 10.6 | 0.8 | — |
| Example 3 | 99.7 | 93.3 | 93.6 | 6.2 | 0.2 | 8.2 |
| Comparative Example 1 | 19.8 | 5.7 | 29.0 | 2.3 | 68.7 | — |
| Comparative Example 2 | 6.5 | 4.2 | 65.1 | 26.7 | 8.2 | — |
| Comparative Example 3 | 22.6 | 1.2 | 5.4 | 6.6 | 88.0 | — |
| Comparative Example 4 | 13.8 | 7.6 | 54.7 | 17.6 | 27.7 | — |
| Comparative Example 5 | 65.8 | 39.3 | 59.7 | 35.7 | 4.6 | 1.4 |
| Comparative Example 6 | 28.9 | 10.6 | 36.8 | 0.0 | 63.2 | 11.4 |
| Comparative Example 7 | 51.4 | 9.0 | 17.4 | 0.8 | 81.8 | 23.8 |

1) Others: Most was analyzed to be acetone.
2) Yield = (methanol conversion) × (selectivity on acetic acid)
3) Leaching (%) represents the results confirming the amount of a metal contained in a liquid phase after a reaction compared to the amount of the metal contained in a catalyst before use by ICP analysis.

The catalysts of Examples 1 to 3 are carbon nitride heterogeneous catalysts containing rhodium provided in the present invention and the amount of rhodium element positioned inside of the support was fixed in a range of 0.5 wt % to 5 wt % based on the total weight of the support. Accordingly, as can be confirmed from Table 1 above, the catalysts exhibited excellent catalytic activities having 88.2 carbon mol % or higher with regard to the conversion of methanol as a reactant and 70.8 mol % or higher with regard to the selectivity on acetic acid.

In contrast, it was confirmed that the catalyst of Comparative Example 1, in which no metal as an active point was incorporated during the formation of a carbon nitride network through rearrangement by thermal modification, and the catalysts of Comparative Examples 2 to 4, in which samarium, nickel, and copper, for which precedent studies as active metals with regard to methanol carbonylation are relatively not available, were positioned inside of the carbon nitride network, showed a significantly reduced conversion of methanol and selectivity on acetic acid, compared to the catalysts of Examples 1 to 3 provided in the present invention.

Additionally, comparing the carbon nitride heterogeneous catalysts of Comparative Examples 5 and 6, in which palladium, ruthenium, and iridium, which are known as showed a trend of having extremely low conversion of methanol and selectivity on acetic acid in reaction conditions for a much easier operation of the process suggested in the present invention instead of the existing high-temperature high-pressure reaction conditions, unlike the results shown in the previous study [*Coordination Chemistry Reviews*, 243 (2003), 125-142].

As such, the carbon nitride containing rhodium suggested in the present invention exhibited an industrial advantage in that the carbon nitride containing rhodium can prepare acetic acid with high yield in low temperature and pressure conditions, which enables less energy consumption and easy operation, compared to the existing high-temperature high-pressure conditions.

With regard to the stability of catalysts, in order to quantitatively confirm the components remaining in the liquid product due to the leaching of the metal as an active material during the progress of the reaction, the experimental results obtained using the above catalysts were subjected to ICP analysis. For this purpose, only the results of the catalysts of Comparative Examples 6 and 7, in which the yields of acetic acid were 10 mol % or higher, and the catalyst of Example 3, in which equal weight parts of rhodium metal were contained, were selected and analyzed. As a result, Comparative Example 5 showed a leaching of palladium (1.4 wt %) in a liquid phase, Comparative Example 6 showed a leaching of ruthenium (11.4 wt %), and Comparative Example 7 showed a leaching of iridium (23.8 wt %).

However, Example 3 showed a leaching of rhodium (8.2 wt %) and the catalytic activity and degree of leaching in the carbon nitride containing rhodium and palladium suggested in the present invention were shown to decrease, comparing with the results of the degree of leaching of active metals in other Comparative Examples.

Meanwhile, in FIG. 1, the selectivity on acetic acid according to the amount of rhodium element contained inside of the carbon nitride in the reaction of the rhodium-containing carbon nitride heterogeneous catalyst (Examples 1 to 3) and the acetic acid yield in the heterogeneous catalyst reactions containing other metals inside of the carbon nitride support (Comparative Examples 1 to 7) were compared and diagrammed into a graph.

According to FIG. 1, it was confirmed that the rhodium-containing carbon nitride heterogeneous catalyst, in which rhodium is positioned in the carbon nitride support in an amount of 0.5 wt % to 5 wt % has higher catalytic activity, compared to g-$C_3N_4$, Sm-g-$C_3N_4$, Ni-g-$C_3N_4$, Cu-g-$C_3N_4$, Pd-g-$C_3N_4$, Ru-g-$C_3N_4$, and Ir-g-$C_3N_4$ heterogeneous catalysts.

Experimental Example 2: Characteristics of Rh-g-$C_3N_4$

Figure 2:
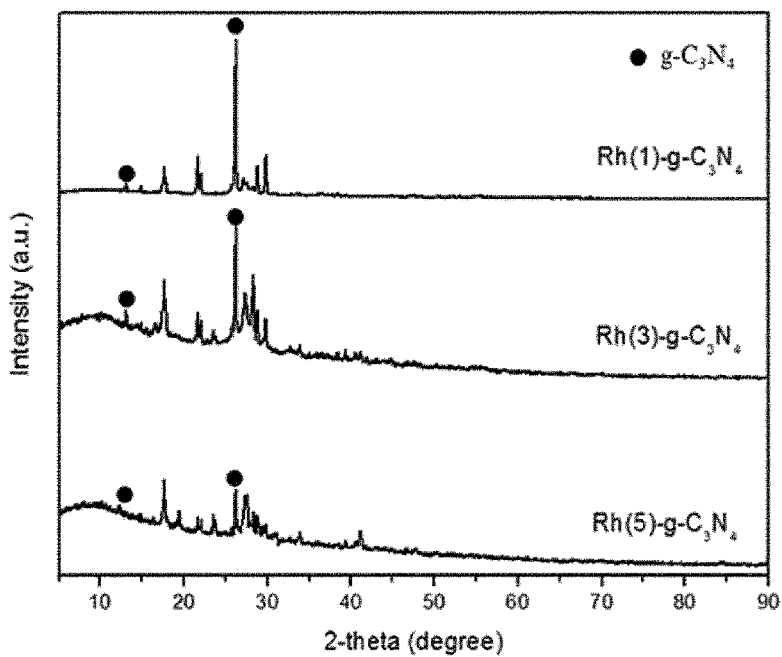
FIG. 2 shows X-ray diffraction (XRD) graph of heterogeneous Rh-g-$C_3N_4$ catalysts according to the present invention.

The heterogeneous Rh-g-$C_3N_4$ catalysts such as Rh(1)-g-$C_3N_4$, Rh(3)-g-$C_3N_4$ and Rh(5)-g-$C_3N_4$ were characterized by X-ray diffraction (XRD) and X-ray photoelectron spectroscopy. AS shown in FIG. 2 and FIG. 3, the Rh nanoparticles was well dispersed in the matrices of g-$C_3N_4$ and the Rh nanoparticles were mainly existing as metallic state, which were confirmed by insignificant XRD peaks of the Rh species and characteristic binding energies or Rh species from XPS analysis. In addition, the well dispersed Rh metals were confirmed by TEM images as shown in FIG. 4.

Experimental Example 3: Activity Comparison of Rh(5)-g-$C_3N_4$ with Simply Impregnated Rh(5)/g-$C_3N_4$ Rh-incorporated g-$C_3N_4$ (Rh-g-$C_3N_4$) as shown in Example 3 showed a higher AA yield with the value of 93.3%, where the Rh metals were highly dispersed in the matrices of the g-$C_3N_4$. The Rh-g-$C_3N_4$ catalyst also showed a better catalytic performance than the simply impregnated Rh(5)/g-$C_3N_4$ prepared by a wet-impregnation method with the less AA yield of 63.2% as shown in Table 2. In addition, a less amount of leached Rh metal was observed on the Rh-g-$C_3N_4$ compared to the impregnated Rh(5)/g-$C_3N_4$ due to a higher dispersion of the Rh metals in the matrices of g-$C_3N_4$ on the most active and stable Rh-g-$C_3N_4$ as shown in Table 3.

TABLE 2

| Catalyst | Conv. (MeOH mol %) | Selectivity (mol %) AcOH | Selectivity (mol %) MeOAc | Yield (AcOH mol %) | Byproduct |
|---|---|---|---|---|---|
| Rh(5)/g-$C_3N_4$ | 99.5 | 63.5 | 36.5 | 63.2 | |
| Rh(5)-g-C3N$_4$ | 99.7 | 93.6 | 6.2 | 93.3 | Acetone 0.2% |

TABLE 3

| Catalyst | Leaching amounts (wt %) |
|---|---|
| Rh(5)/g-$C_3N_4$ | 39.7 |
| Rh(5)-g-$C_3N_4$ | 8.2 |

The invention claimed is:

1. A composite catalyst for carbonylation of methanol to acetic acid, comprising a carbon nitride support and rhodium dispersed in the network of the carbon nitride support to reduce the leaching level of the rhodium in the methanol carbonylation.

2. The composite catalyst of claim 1, wherein the rhodium is contained in an amount of 0.1 wt % to 10 wt % based on the total weight of the carbon nitride.

3. The composite catalyst of claim 1, wherein the composite catalyst has a specific surface area in a range of 0.5 m$^2$/g to 100 m$^2$/g.

4. The composite catalyst of claim 1, wherein the carbon nitride is selected from the group consisting of graphite carbon nitride, α-carbon nitride, β-carbon nitride, cubic carbon nitride, pseudocubic carbon nitride, and combinations thereof.

5. A method of preparing a composite catalyst comprising carbon nitride support and rhodium dispersed therein, comprising heating a rhodium precursor and melamine resin serving as a carbon source at a temperature of 500° C. to 550° C. in a nitrogen atmosphere.

6. The method of claim 5, wherein the rhodium precursor is selected from the group consisting of rhodium chloride, rhodium nitrate, dichloro tetracarbonyl dirhodium, (acetylacetonato)dicarbonyl rhodium, acetylacetonato bis(ethylene)rhodium, dicarbonyl(pentamethyl-cyclopentadienyl)rhodium, and combinations thereof.

7. The method of claim 5, wherein the carbon nitride is selected from the group consisting of graphite carbon nitride, α-carbon nitride, β-carbon nitride, cubic carbon nitride, pseudocubic carbon nitride, and combinations thereof.

8. A method of preparing acetic acid, comprising reacting at a temperature of 50° C. to 200° C. by injecting a carbon monoxide-containing gas into an methanol containing solution at a pressure of 10 bar to 200 bar in the presence of the composite catalyst according to claim 1.

9. The method of claim 8, wherein the methanol containing solution comprises methanol as a reactant and iodomethane as co-catalyst and water.

10. The method of claim 9, wherein the methanol:iodomethane:water mixing ratio is as follows:
10 parts by weight to 80 parts by weight of methanol;
10 parts by weight to 60 parts by weight iodomethane; and
10 parts by weight to 30 parts by weight water.

11. The method of claim 8, wherein the carbon monoxide-containing gas is a mixed gas of carbon monoxide and nitrogen.

12. The method of claim 11, wherein the mixing molar ratio between carbon monoxide and nitrogen is as follows
7 parts by mole to 9 parts by mole of carbon monoxide; and
1 part by mole to 3 parts by mole of nitrogen.

13. The method of claim 8, wherein, in the molar ratio between methanol and carbon monoxide is maintained in a range of 0.6 to 10.0 based on 1 mole of methanol.

14. A composite catalyst, prepared by the method of claim 5.

15. A method of producing acetic acid by carbonylating methanol in the presence of a composite catalyst comprising a carbon nitride support and rhodium dispersed therein.

16. The method of claim 15, wherein the rhodium is contained in an amount of 0.1 wt % to 10 wt % based on the total weight of the carbon nitride.

17. The method of claim 15, wherein the composite catalyst has a specific surface area in a range of 0.5 m$^2$/g to 100 m$^2$/g.

18. The method of claim 15, wherein the carbon nitride is at least one kind selected from the group consisting of graphite carbon nitride, α-carbon nitride, β-carbon nitride, cubic carbon nitride, pseudocubic carbon nitride, and combinations thereof.

\* \* \* \* \*